United States Patent [19]
Schricker

[11] Patent Number: 4,857,332
[45] Date of Patent: Aug. 15, 1989

[54] COMPOSITION AND METHOD FOR INCREASING MILK FAT PRODUCTION IN RUMINANTS

[75] Inventor: Brian R. Schricker, Terre Haute, Ind.

[73] Assignee: Pitman-Moore, Inc., Terre Haute, Ind.

[21] Appl. No.: 200,454

[22] Filed: May 31, 1988

[51] Int. Cl.$^4$ .............................................. A23K 1/17
[52] U.S. Cl. .................................... 424/442; 426/2; 426/623; 426/630; 426/635; 426/807
[58] Field of Search ................ 424/442; 426/658, 809, 426/807, 623, 630, 635, 2

[56] References Cited

U.S. PATENT DOCUMENTS

| | | | |
|---|---|---|---|
| 3,421,898 | 1/1969 | Erwin et al. | 426/807 |
| 3,577,513 | 5/1971 | Roebuck et al. | 426/465 |
| 4,027,043 | 5/1977 | Schroeder et al. | 426/69 |
| 4,171,385 | 10/1979 | Skoch et al. | 426/658 |
| 4,171,386 | 10/1979 | Skoch et al. | 426/655 |
| 4,452,779 | 6/1984 | Cockerill | 424/156 |
| 4,540,577 | 9/1985 | Hunt et al. | 424/153 |

OTHER PUBLICATIONS

Schneider et al., "Influence of Dietary Sodium and Potassium Bicarbonate and Total Potassium on Heat-Stressed Lactating Dairy Cows", *Journal of Dairy Science*, vol. 67, pp. 2546–2553 (1984).

Primary Examiner—Thurman K. Page
Assistant Examiner—P. L. Prater
Attorney, Agent, or Firm—Wendell Ray Guffey; Thomas L. Farquer

[57] ABSTRACT

A composition for synergistically increasing milk fat production in ruminants comprising (1) pellets which comprise an antacid selected from the group consisting of sodium and magnesium antacids and an electrolyte selected from the group consisting of potassium, sodium, and chlorine containing electrolytes, said pellets containing potassium, sodium, and chlorine in a weight ratio of from about 1.5 to about 1.8 parts of potassium and from about 1.2 to about 1.5 parts of chlorine per part of sodium, said potassium being present in sufficient amount to provide from about 0.8 to about 1 weight parts of potassium per weight part of any magnesium present and (2) sodium bicarbonate.

20 Claims, No Drawings

COMPOSITION AND METHOD FOR INCREASING MILK FAT PRODUCTION IN RUMINANTS

This invention relates generally to compositions and methods for increasing milk fat production in ruminants and particularly to compositions and methods for using rumen buffers, electrolytes, and sodium bicarbonate to synergistically increase milk fat production in lactating dairy cows.

BACKGROUND OF THE INVENTION

Current ruminant feeds and feeding practices rely heavily on readily fermentable carbohydrates and chopped, ensiled forages. Such feeds generate acids in the rumen which are not completely counterbalanced by dietary or endogenous bases and buffers. Under more acidic conditions, the population of microorganisms found in the rumen is less desirable than the population found under less acidic or neutral conditions. Under these less acidic or neutral conditions, rumen microorganisms produce more fatty acids which can be used by the lactating animal to produce milk fat.

It is known that sodium bicarbonate and magnesium oxide, alone or in combination, are effective in increasing the milk and/or milk fat production of animals fed on high acid-producing diets. Chalupa and Kronfeld, 1983, Animal Nutrition and Health, May—June, 50; Erdman, et al. 1982, Journal of Dairy Science, 65, 712; Erdman, et al. 1980, Journal of Dairy Science, 63, 923; and Kilmer et al. 1980, Journal of Dairy Science, 63, 2026. However, these additives have the undesirable effects of temporarily reducing the feed intake and decreasing the serum levels of potassium and magnesium. Improved methods for increasing milk fat production using new compositions and methods are therefore continually needed.

SUMMARY OF THE INVENTION

It is, therefore, an object of the present invention to provide a composition for increasing milk fat production in ruminants.

It is another object of the present invention to provide a method for increasing milk fat production in ruminants.

It is a further object of the present invention to provide a feed composition suitable for increasing milk fat production in ruminants.

This and other objects are achieved by feeding a composition comprising (1) pellets which comprise an antacid selected from the group consisting of sodium and magnesium antacids and electrolytes selected from the group consisting of potassium, sodium, and chlorine containing electrolytes and (2) sodium bicarbonate to ruminants in amounts sufficient to synergistically increase milk fat production. The pellets contain potassium, sodium, and chlorine in a weight ratio of from about 1.5 to about 1.8 parts of potassium and from about 1.2 to about 1.5 parts of chlorine per part of sodium. The pellets contain potassium in sufficient amounts to provide from about 0.8 to about 1 weight parts of potassium per weight part of any magnesium in the pellets.

In the preferred embodiment, the composition is formed by mixing the pellets and sodium bicarbonate at a ratio of about 1:8 to about 8:1 by weight and fed directly to the ruminant in amounts from about 0.5–2 pounds/ruminant/day to synergistically increase milk fat production.

In the most preferred embodiment, a composition of the pellets and sodium bicarbonate or the pellets and sodium bicarbonate individually are admixed with a feed composition in amounts of from about 0.5–5% pellets by weight and from about 0.1–1.5% sodium bicarbonate by weight and the feed composition is fed to the ruminant to synergistically increase milk fat production.

Other objects, advantages, and novel features of the present invention will become apparent from the following detailed description of the invention.

DETAILED DESCRIPTION OF THE INVENTION

The composition of the present invention has two components: (1) pellets which comprise an antacid selected from the group consisting of sodium and magnesium antacids and an electrolyte selected from the group consisting of potassium, sodium, and chlorine containing electrolytes and (2) sodium bicarbonate ($NaHCO_3$). The pellets contain potassium, sodium, and chlorine in a weight ratio of from about 1.5 to about 1.8 parts of potassium and from about 1.2 to about 1.5 parts of chlorine per part of sodium. The pellets contain potassium in sufficient amounts to provide from about 0.8 to about 1 weight parts of potassium per weight part of any magnesium in the pellets. The composition is fed to ruminants to synergistically increase milk fat production; the combination of the pellets and sodium bicarbonate increases milk fat production more than the sum of the increases in milk fat production for the pellets and sodium bicarbonate when fed to the ruminants separately.

The composition is formed by admixing the pellets and sodium bicarbonate, preferably by admixing the components just prior to feeding the composition to the ruminant. Alternatively, when feeding the composition in combination with the ruminant's feed, the pellets and sodium bicarbonate can be mixed individually with the feed to form the composition. The pellets and sodium bicarbonate are admixed at a ratio of about 1:8 to about 8:1 by weight.

The pellets are made in sizes suitable for administration to the ruminant by agglomerating a combination of antacids and electrolytes which have been commuted to the desired particle size and mixed in the appropriate ratio. Generally, the pellet components are reduced to a particle size of less than about 100 Tyler mesh and agglomerated to produce pellets having a size of at greater than about plus 48 Tyler mesh.

The weight ratio among elements must be within about 10% of 1:65:1:1.35:1.88 of K:Na:Cl:Mg, that is to say the pellets should contain from about 1.5 to about 1.8 parts of potassium and from about 1.2 to about 11.5 parts of chlorine per part of sodium. The magnesium is not required, but if it is supplied in the antacid, it should be balanced by the other elements in the appropriate ratio. That is to say that magnesium:potassium should be within about 10% of 1.14:1, or from about 0.8 to about 1 weight parts of potassium per weight part of any magnesium present. The amounts and types of electrolytes to be added to the antacid to provide the specified ratios can be readily chosen by one skilled in the art.

In the preferred embodiment, the antacid and electrolyte components of the pellets are agglomerated to form pellets having a size of at least about plus 48 Tyler mesh, preferably from about 48 to about 8 Tyler mesh. The rate at which the pellets dissolve in the rumen or stomach is greatly decreased if the pellet components are ground to a specific particle size prior to agglomeration; generally the particle size of the components should be reduced to less than 100 Tyler mesh, preferably to less than 250 Tyler mesh.

The antacid and electrolyte sources which are used to make the pellets of the present invention can be any feed grade or better quality material which is not toxic to the animal. The antacids which may be used include magnesium oxide, sodium bicarbonate, dolomite, sodium hydroxide, calcium hydroxide, calcium carbonate, magnesium carbonate, sodium carbonate, northupite and mixtures thereof. Suitable electrolyte sources which may be used in the practice of the invention are any that are conventionally used as animal or human nutritional supplements, including potassium chloride, langbeinite, potassium bicarbonate, arcanite, potassium hydroxide, potassium phosphates, potassium carbonate, sodium chloride, and mixtures thereof.

Surprisingly, agglomeration not only slows the rate of dissolution of the pellets in the rumen, but also causes a greater total pH change in the rumen than unagglomerated material. Reasons for the alteration in the antacid characteristics of the pellets are not precisely known. However, the preferred method of preparing the pellets, i.e., grinding of the ingredients to achieve a substantially uniform particle size of less than 100 Tyler mesh and agglomerating, results in a chemical reaction.

Generally, there is a range of about 5% by weight of the dry ingredients of liquid which may be employed for any particular composition which will achieve pellets of appropriate sizes and durability. This range will vary with the particular materials employed in the composition and the size of the materials. The range for a particular composition can be determined by routine testing. Too much liquid will lead to pellets which are too large and which are wet and sticky. Too little water will lead to particles which are too small, and are additionally weak and crumbly. Generally, as the fineness of the particles increases, more liquid is required to agglomerate properly. Liquids other than water may be used, for example, a solution of choline chloride may be used advantageously. Amounts of water or other liquid which are added to form pellets are generally between about 5 and 20% by weight of the other ingredients. This proportion of liquid to solids produces pellets of appropriate dimensions.

In addition, when binders, such as starch, hydraulic cement, and clay binders, are added to the pellets, the resistance of the pellets to breakage and abrasion is increased. In one preferred embodiment bentonite (a clay binder) is added to the formulation for the pellets. Suitable amounts of bentonite are generally less than about 5% by weight, and preferably about 2%. Further, the addition of certain widely used components such as molasses may have an adverse effect on the dissolution characteristics of the pellets, causing the solubilization rate to increase. Conversely components such as cement and bentonite decrease the rate of solubilization.

The initial ingredients may be ground individually or together to achieve good mixing. This may be accomplished by any of the means known in the art, such as using ball mills, jet mills, pulverizers and hammer mills. Any means which will achieve the desired degree of fineness is suitable. A disc pelletizer is well-suited for carrying out the agglomeration of the ground materials, although other apparati may be used. The agglomeration of the ground ingredients may be performed by drum, disc, cone or pan pelletizers, pressure compaction, extrusion, or any other means known in the art.

After the pellets have been formed by agglomeration, they may be dried at either ambient or higher temperatures to remove moisture. A vibrating fluidized bed dryer is suitable for this purpose. The dried particles can be screened to ensure that they are of the proper dimensions. Oversized granules may be discarded or reduced in size, for example, by means of a knife granulator.

After the processing involved in producing the pellets of the present invention, new compounds may be found, indicating that a chemical reaction has occurred. For example, when potassium chloride, langbeinite, magnesium oxide and sodium bicarbonate are present in the initial mixture, northupite has been detected by means of x-ray diffraction in the pelletized product as a major reaction product. Thus, the method of the present invention provides a means of making northupite. Arcanite has also been tentatively identified in the product.

The pellets, method for producing the pellets, advantages of the pellets, and the experimental work showing those advantages, particularly with respect to milk fat production, are fully described in pending patent application Ser. No. 877,313, incorporated herein by reference. The pellets are sold by Pitman-Moore, Inc., 1401 South Third Street, Terre Haute, IN under the trademark RUMEN-MATE ®.

The sodium bicarbonate can be any feed grade sodium bicarbonate or feed grade material containing sodium bicarbonate such as sodium sesquicarbonate and trona. Feed grade sodium bicarbonate and materials containing sodium bicarbonate are available from numerous commercial sources; sources known to those skilled in the art.

According to the method of the present invention, the pellets and sodium bicarbonate are fed to ruminants to synergistically increase milk fat production. Because of the synergistic interaction between the pellets and the sodium bicarbonate, the amount of antacid and electrolyte fed to the animal can be decreased resulting in a lower feeding cost and decreasing any undesirable side effects associated with feeding large amounts of the compounds.

The pellets and sodium bicarbonate can be mixed to form the composition of the present invention and fed directly to the ruminant in amounts sufficient to synergistically increase milk fat production. Generally, the present method comprises feeding from about 0.5–2 pounds/ruminant/day of a composition containing the pellets and sodium bicarbonate at a ratio of about 1:8 to about 8:1 by weight.

Preferably, the pellets and sodium bicarbonate are mixed to form the composition of the present invention and blended with ordinary feed compositions or are blended individually with ordinary feed compositions in amounts sufficient to synergistically increase milk fat production. An animal feed composition may be prepared containing the usual nutritionally-balanced feed containing quantities of carbohydrates, proteins, fiber, vitamins and minerals, together with the pellets and sodium bicarbonate in accordance with the present invention. Some of the usual dietary elements included in animal feed compositions are grains, such as ground grain and grain byproducts, animal protein substances, such as those found in fish meal and meat scraps, vegetable proteins, like soybean oil meal or peanut oil meal; vitamins and vitamin-containing materials, e.g., vitamin A and D mixtures, riboflavin supplements and other vitamin B complex members; and bone meal and limestone to provide minerals. A type of conventional feed material for use with cattle includes alfalfa hay and ground corncobs together with supplementary vitamins and vitamin-containing substances if desired. The pellets and sodium bicarbonate according to the present invention are admixed with the feed composition in amounts of from about 0.5-5%, preferably from about 2-4%, and from about 0.1-1.5%, preferably 0.25-1%, respectively.

U.S. Pat. No. 3,778,508, incorporated herein by reference, discloses basal feed compositions for sheep and cattle. Many other such compositions are well known to those skilled in the art.

The composition can be fed to any lactating ruminant, particularly cattle and sheep, to synergistically increase milk fat production.

The invention having been generally described, the following examples are given as particular embodiments of the invention and to demonstrate the practice and advantages thereof. It is understood that the examples are given by way of illustration and are not intended to limit the specification or the claims to follow in any manner.

EXPERIMENTAL PROCEDURE

EXAMPLE 1

Sixteen multiparous Holstein cows in midlactation were used in a 6×6 Latin square design replicated 2 times. Each period consisted of a 7-day adaptation period and a 14-day data collection period. The basal ration (Table 1) was composed of approximately 40% corn silage and 60% concentrate. All rations were formulated to meet or exceed NRC (1978) requirements. The dietary treatments were:

a. basal ration
b. 0.8% sodium bicarbonate
c. 0.8% sodium bicarbonate plus 0.5% magnesium oxide
d. 0.5% magnesium oxide
e. 2.65% RUMEN-MATE ®
f. 1.85% RUMEN-MATE ® plus 0.8% sodium bicarbonate Additions to the basal ration were made on a dry matter basis and substituted for corn.

Upon initiation of the experiment, the cows were fed their respective complete mixed rations twice daily after the forage and concentrate portions were thoroughly mixed for each individual cow. Feed refusals were collected and weighed just prior to the next feeding and daily feed offered was adjusted as needed so that there were 10% feed refusals (as feed) during each 24 hour period. Samples of individual dietary treatment concentrate mixes were taken each time a new mix was made and forages were sampled 3 times per week throughout the experiment. Forage samples were analyzed immediately for dry matter so that appropriate adjustments in the forage to concentrate ratio were made semi-weekly. Fresh water was provided ad libitum.

Milk production was measured at each milking (twice daily) and yield data for the final 14 days of each experimental period was used to estimate effect of treatment on milk composition. Milk samples from each cow were taken on days 2, 3, 8, 9, 14, 15, 20, and 21 of each period for milk fat composition analysis. The results are shown in Table 2.

Referring to Table 2, milk fat, as a percent and as total kg produced per day, was increased synergistically by feeding the pellets (RUMEN-MATE ®) and sodium bicarbonate in combination. The addition of $NaHCO_3$ increased milk fat yield 0.02 kg/day while RUMEN-MATE ® increased milk fat yield 0.03 kg/day. However, the combination increased yield 0.06 kg/day. Similarly, 4% fat corrected milk (FCM) was increased by $NaHCO_3$ and slightly by RUMEN-MATE ® (0.3 and 0.1 kg/day, respectively) but the combination increased 4% FCM to a greater level (1 kg/day). Therefore, the combination of $NaHCO_3$ and RUMEN-MATE ® results in a synergistic affect on milk fat production and 4% FCM and is not just an additive affect on these parameters.

Obviously many modifications and variations of the present invention are possible in light of the above teachings. It is therefore to be understood that within the scope of the appended claims the invention may be practiced otherwise than as specifically described.

TABLE 1

Composition of Basal Ration

| Ingredient | Diet (% Dry Matter) |
| --- | --- |
| Corn silage | 39.52 |
| Ground corn | 35.08 |
| Soybean meal | 22.42 |
| Dicalcium phosphate | 1.06 |
| ADE vitamin mix | 0.11 |
| Trace mineral mix | 0.01 |
| $MgSO_4$ | 1.15 |
| NaCl | 0.37 |

TABLE 2

Effect of Dietary Buffers Alone and in Combination on Milk Production

| Treatment | Milk yield (kg/day) | Milk fat (kg/day) | % | 4% FCM (kg/day) |
| --- | --- | --- | --- | --- |
| Basal ration | 30.7 | 0.92 | 3.08 | 26.1 |
| 0.8% $NaHCO_3$ | 30.7 | 0.94 | 3.10 | 26.4 |
| 2.65% RUMEN-MATE ® (RM) | 29.8 | 0.95 | 3.21 | 26.2 |
| 0.8% $NaHCO_3$ + 2.65% RM | 31.0 | 0.98 | 3.19 | 27.1 |
| 0.5% MgO | 30.4 | 0.94 | 3.12 | 26.3 |
| 0.5% MgO + 0.8% $NaHCO_3$ | 30.7 | 0.99 | 3.28 | 27.1 |

What is claimed is:

1. A composition for synergistically increasing milk fat production in ruminants, comprising:
pellets which comprise an antacid selected from the group consisting of sodium and magnesium antacids and an electrolyte selected from the group consisting of potassium, sodium, and chlorine containing electrolytes, said pellets containing potassium, sodium, and chlorine in a weight ratio of from about 1.5 to about 1.8 parts of potassium and from about 1.2 to about 1.5 parts of chlorine per part of sodium, said potassium being present in sufficient amount to provide from about 0.8 to about 1 weight parts of potassium per weight part of any magnesium present; and
sodium bicarbonate.

2. The composition of claim 1 having a ratio of pellets to sodium bicarbonate of from about 1:8 to about 8:1 by weight.

3. The composition of claim 1 wherein said pellets have a size of greater than about plus 48 Tyler mesh.

4. The composition of claim 1 wherein said pellets have been formed by agglomeration of components having a particle size of less than about 100 Tyler mesh.

5. The composition of claim 1 wherein said pellets have a size of from about 48 to about 8 Tyler mesh, said pellets having been formed by agglomeration of components having a particle size of less than from about 100 to about 250 Tyler mesh.

6. A feed composition suitable for synergistically increasing milk fat production in ruminants, comprising:
   a nutritionally balanced feed; and
   a milk fat production increasing amount of a composition comprising pellets which comprise an antacid selected from the group consisting of sodium and magnesium antacids and an electrolyte selected from the group consisting of potassium, sodium, and chlorine containing electrolytes, said pellets containing potassium, sodium, and chlorine in a weight ratio of from about 1.5 to about 1.8 parts of potassium and from about 1.2 to about 1.5 parts of chlorine per part of sodium, said potassium being present in sufficient amount to provide from about 0.8 to about 1 weight parts of potassium per weight part of any magnesium present, and sodium bicarbonate admixed with said feed.

7. The feed composition of claim 6 containing said pellets in amounts of from about 0.5–5% by weight and sodium bicarbonate in amounts of from about 0.1–1.5% by weight.

8. The feed composition of claim 6 having a ratio of pellets to sodium bicarbonate of from about 1:8 to about 8:1 by weight.

9. The feed composition of claim 6 wherein said pellets have a size of greater than about plus 48 Tyler mesh.

10. The feed composition of claim 6 wherein said pellets have been formed by agglomeration of components having a particle size of less than about 100 Tyler mesh.

11. The feed composition of claim 6 wherein said pellets have a size of from about 48 to about 8 Tyler mesh, said pellets having been formed by agglomeration of components having a particle size of less than from about 100 to about 250 Tyer mesh.

12. A method for synergistically increasing milk fat production in ruminants, comprising:
   feeding a milk fat production increasing amount of a composition comprising pellets which comprise an antacid selected from the group consisting of sodium and magnesium antacids and an electrolyte selected from the group consisting of potassium, sodium, and chlorine containing electrolytes, said pellets containing potassium, sodium, and chlorine in a weight ratio of from about 1.5 to about 1.8 parts of potassium and from about 1.2 to about 1.5 parts of chlorine per part of sodium, said potassium being present in sufficient amount to provide from about 0.8 to about 1 weight parts of potassium per weight part of any magnesium present, and sodium bicarbonate to said ruminants.

13. The method of claim 12 wherein said composition has a ratio of pellets to sodium bicarbonate of from about 1:8 to about 8:1 by weight.

14. The method of claim 12 wherein said pellets have a size of greater than about plus 48 Tyler mesh.

15. The method of claim 12 wherein said pellets have been formed by agglomeration of components having a particle size of less than about 100 Tyler mesh.

16. The method of claim 12 wherein said pellets have a size of from about 48 to about 8 Tyler mesh, said pellets having been formed by agglomeration of components having a particle size of less than from about 100 to about 250 Tyler mesh.

17. The method of claim 12 wherein said composition is fed in amounts of from about 0.5–2 pounds/ruminant/day of a composition containing said pellets and sodium bicarbonate at a ratio of about 1:8 to about 8:1.

18. The method of claim 12 wherein said composition is administered in a feed composition, said feed composition further comprising:
   a nutritionally balanced feed; and
   a milk fat production increasing amount of a composition comprising pellets which comprise an antacid selected from the group consisting of sodium and magnesium antacids and an electrolyte selected from the group consisting of potassium, sodium, and chlorine containing electrolytes, said pellets containing potassium, sodium, and chlorine in a weight ratio of from about 1.5 to about 1.8 parts of potassium and from about 1.2 to about 1.5 parts of chlorine per part of sodium, said potassium being present in sufficient amount to provide from about 0.8 to about 1 weight parts of potassium per weight part of any magnesium present, and sodium bicarbonate admixed with said feed.

19. The method of claim 12 wherein said ruminants are selected from the group consisting of cattle and sheep.

20. The method of claim 19 wherein said ruminants are lactating dairy cows.

* * * * *